(12) United States Patent
Blackwood et al.

(10) Patent No.: US 7,329,872 B2
(45) Date of Patent: Feb. 12, 2008

(54) SPECTRAL ANALYSIS METHOD FOR DETECTING AN ELEMENT

(75) Inventors: Larry G. Blackwood, Idaho Falls, ID (US); Andrew J. Edwards, Idaho Falls, ID (US); James K. Jewell, Idaho Falls, ID (US); Edward L. Reber, Idaho Falls, ID (US); Edward H. Seabury, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 30 days.

(21) Appl. No.: 11/231,141

(22) Filed: Sep. 19, 2005

(65) Prior Publication Data
US 2007/0063143 A1    Mar. 22, 2007

(51) Int. Cl.
*G01F 23/00* (2006.01)
*G01J 1/42* (2006.01)

(52) U.S. Cl. .................................. 250/358.1; 250/372
(58) Field of Classification Search ................ 250/372, 250/358.1
See application file for complete search history.

(56) References Cited

U.S. PATENT DOCUMENTS

| 6,215,122 B1* | 4/2001 | Clifford et al. ............. 250/369 |
| 6,791,089 B1* | 9/2004 | Caffrey et al. ........... 250/358.1 |
| 2002/0150194 A1* | 10/2002 | Wielopolski et al. ....... 376/160 |

* cited by examiner

*Primary Examiner*—David Porta
*Assistant Examiner*—Carolyn Igyarto
(74) *Attorney, Agent, or Firm*—Wells St. John P.S.

(57) ABSTRACT

A method for detecting an element is described and which includes the steps of providing a gamma-ray spectrum which has a region of interest which corresponds with a small amount of an element to be detected; providing nonparametric assumptions about a shape of the gamma-ray spectrum in the region of interest, and which would indicate the presence of the element to be detected; and applying a statistical test to the shape of the gamma-ray spectrum based upon the nonparametric assumptions to detect the small amount of the element to be detected.

11 Claims, 6 Drawing Sheets

SPECTRAL ANALYSIS METHOD FOR DETECTING AN ELEMENT

GOVERNMENT RIGHTS

The United States Government has certain rights in this invention pursuant to Contract No. DE-AC07-05ID14517 between the United States Department of Energy and Battelle Energy Alliance, LLC.

TECHNICAL FIELD

The present invention relates to a method for detecting an element, and more specifically to methodology which is utilized to improve the detection of small amounts of elements in a Sodium Iodide spectra, and which is indicative of the presence of contraband, such as explosives, and the like.

BACKGROUND OF THE INVENTION

As of late, various methodology and devices have been developed, or are currently under development for the detection of explosives, and other contraband of various quantities, and which might be utilized in terrorist acts. Currently, vehicles and containers entering restricted areas, such as military bases, courtrooms, and facilities for public transportation are checked for contraband by means of physical search, x-ray, vapor detection, or canine units who are deployed by law enforcement or other military personnel. Heretofore, various automatic spectral analysis routines have been developed, and which are useful in the detection of explosives which might be concealed in vehicles, containers and the like. Such systems have included methodology and apparatus for interrogating a vehicle or container with neutrons provided by a neutron generator and thereafter collecting the gamma energy generated by the presence of any explosive substance by utilizing sodium iodide detectors. In these earlier devices, and methodology, the typical gamma-ray spectrum collected was then analyzed based upon Gaussian peak fitting, including peak deconvolution in order to identify the explosive substance.

While this methodology and the devices, which have implemented the same, have worked with some degree of success, they have had shortcomings which have detracted from their usefulness. More specifically, the standard analysis methodology as noted above, including Gaussian peak fitting and peak deconvolution do not produce reliable results when the Sodium Iodide spectra is collected from measurements of relatively small quantities of explosives at stand-off distances of up to six feet. As should be understood, the detection of relatively small quantities of explosives is important in the identification of potential terrorist threats, and perpetrators, as well as in the conduct of various investigations regarding the illegal use of explosives.

Therefore, a method for detecting an element which avoids the shortcomings attendant with the prior art methodology and devices utilized heretofore is the subject matter of the present application.

SUMMARY OF THE INVENTION

A first aspect of the present invention is to provide a method for detecting an element which includes providing a gamma-ray spectrum which has a region of interest which corresponds with a small amount of an element to be detected; providing nonparametric assumptions about a shape of the gamma-ray spectrum in the region of interest, and which would indicate the presence of the element to be detected; and applying a statistical test to the shape of the gamma-ray spectrum based upon the nonparametric assumptions to detect the small amount of the element to be detected.

Another aspect of the present invention is to provide a method for detecting an element which includes the steps of providing a gamma-ray spectrum; defining a region of interest within the gamma-ray spectrum which corresponds with an element which is to be detected; defining a first channel of the region of interest which has a number of counts; defining a last channel of the region of interest which has a number of counts; calculating the number of counts of a plurality of channels which are located adjacent to the first and last channels; calculating background counts in the region of interest for the element to be detected based, at least in part, upon the number of counts in the plurality of channels which are located adjacent to the first and last channels; calculating the total counts in the region of interest; calculating net counts due to the element of interest by subtracting the background counts from the total counts in the region of interest; calculating a statistic from the net and background counts in the region of interest for the element to be detected; and calculating a probability value based upon the calculated statistic to derive a detection confidence factor indicating the degree of assurance that the element to be detected is present.

Yet further, another aspect of the present invention relates to a method for detecting an element which includes the steps of providing a gamma-ray spectrum; defining a region of interest within the gamma-ray spectrum which corresponds with an element to be detected; defining a first channel of the region of interest; defining a last channel of the region of interest; fitting a quadratic equation, having a quadratic term, to the region of interest which is defined between the first and last channels; calculating a statistical significance of the quadratic term which is derived from the quadratic equation; and calculating a probability value for the statistical significance of the quadratic term to determine a confidence value which relates to the presence of the element to be detected.

Moreover, another aspect of the present invention relates to a method for detecting an element which includes providing a gamma-ray spectrum; defining a region of interest within the gamma-ray spectrum which corresponds with an element to be detected; defining a first channel of the region of interest which has a number of counts; defining a last channel of the region of interest which has a number of counts; fitting a quadratic equation, having a quadratic term, to the region of interest which is defined between the first and last channels; calculating a statistical significance of the quadratic term which is derived from the quadratic equation; calculating a probability value for the statistical significance of the quadratic term to determine the presence of the element to be detected; and comparing the probability value for the statistical significance of the quadratic term with the confidence factor to determine the presence of the element to be detected.

These and other aspects of the present invention will be described in greater detail hereinafter.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

The present invention provides a method for detecting trace amounts of material or elements which might be present and which indicate the presence of an explosive. It should be understood that the present invention, however, is not limited to this purpose, but may be found useful for the detection of trace or larger amounts of different elements and which indicates the presence of other materials.

Figure 1:
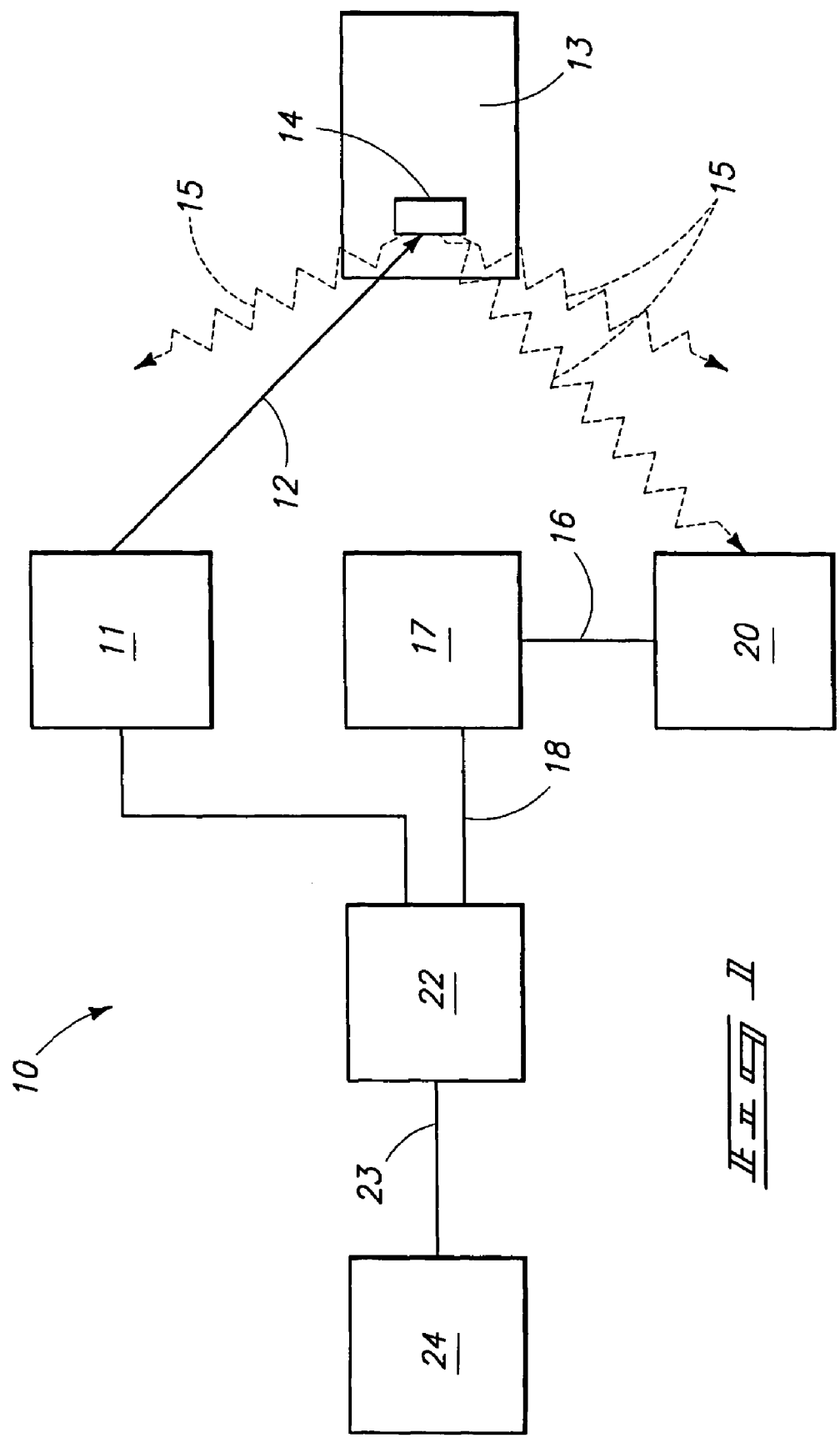
FIG. 1 is a greatly simplified schematic diagram of an arrangement which is useful for practicing the methodology of the present invention.

FIG. 1 shows a greatly simplified depiction of a system or arrangement 10 which is useful in practicing the methodology of the present invention. In the present methodology, the inventors have provided a means for applying various tests to a spectra for the purposes of detecting the presence of an element. The tests which are employed utilize nonparametric assumptions about the shape of the spectral response in a region of interest. As implemented, the present methodology provides a novel means by which an operator can detect small quantities of an element of interest with a high level of detection confidence and with a low level of false positives. Still further, the present methodology allows a system to be built which utilizes considerably fewer Sodium Iodide detectors, that will be described below, and which will operate with quicker throughput while maintaining a high level of detection confidence.

Referring again to FIG. 1, it will be seen that an apparatus for detecting an element and which implements the methodology of the present invention is generally indicated by the numeral 10. The present apparatus 10, which is shown in a very simple schematic fashion includes, as a general matter, a neutron generator 11 which is operable to generate a source or stream of neutrons 12 which are directed towards, or travel in the direction of, a target to be interrogated 13. As seen, the target to be interrogated includes trace amounts of an element to be detected 14. This trace amount of an element to be detected may include elements such as nitrogen which forms an important part of most modern explosives. As should be understood, the neutron generator may be commercially purchased. A commercially suitable neutron generator is a GENIE™ 16-C neutron generator which is available from Sodern, 20 Descartes Avenue, Limeil, Brevannes, France. Other commercially available neutron generators could also be employed. In the illustrated embodiment 14 MeV neutrons are produced. In this regard, the high energy neutrons penetrate the target 13 to be interrogated and interact with any trace amounts of any explosive, for example, which might include nitrogen, which is in or on the target. Some of these neutrons are thermalized within the trace amounts of the element to be detected, or the surrounding material, and are captured by the nitrogen atoms which are present. More specifically, some of the neutrons inelastically scatter off of the various trace elements until they eventually thermalize and are captured. These interactions release signature gamma-rays 15 which are received, and substantially measured by a gamma-ray energy detector 20 which typically comprises a Sodium Iodide detector. Typically, the arrangement 10 will have an array of gamma-ray energy detectors 20. As should be understood, when a neutron is captured by a nitrogen atom that might be incorporated, for example, in an explosive, a 10.8 MeV gamma-ray of energy is released. The gamma-ray energy detector 20 receives this energy and produces an electrical signal output 16, which is then subsequently supplied to a digital electronics system 17 of conventional design. The digital electronics system 17 is operable to generate a gamma-ray spectrum 30 from the received electrical output 16, and further produces an electrical signal output 18 which is supplied to a control system 22. The control system is operable to analyze a gamma-ray spectrum 30 (FIG. 4) from the received electrical output 18, and is further operable to supply a corresponding electrical signal 23 to a display apparatus 24 which provides a message to an operator (not shown) and which indicates the presence of the element 14 to be detected.

Therefore, in one aspect of the present invention the methodology for detecting an element 14 includes the steps of providing a gamma-ray spectrum 30 which is generated by a digital electronics system 17, and which has a region of interest, and which corresponds with a small amount of an element to be detected; providing nonparametric assumptions about a shape of the gamma-ray spectrum in the region of interest, and which would indicate the presence of the element to be detected; and applying a statistical test to the shape of the gamma-ray spectrum based upon the nonparametric assumptions to detect the small amount of the element to be detected.

As discussed above with respect to FIG. 1, the step of providing the gamma-ray spectrum further includes the steps of providing a target to be interrogated 13; and providing a neutron generator 11 which provides a source of neutrons 12; and further interrogating the target with the neutrons. The method further includes the steps of providing a gamma-ray energy detector 20 which has an electrical output 16, and collecting gamma-ray radiation 15 which is emitted by the target 13 following the interrogation of the target with the neutrons 12 with the gamma-ray energy detector 20; and receiving the electrical output of the gamma-ray energy detector 16 to form the gamma-ray spectrum 30 with a digital electronics system 17. The arrangement as shown is particularly useful in detecting trace amounts of nitrogen. In the arrangement as seen in FIG. 1, the gamma-ray energy detector 20 is a Sodium Iodide detector.

Figure 2:
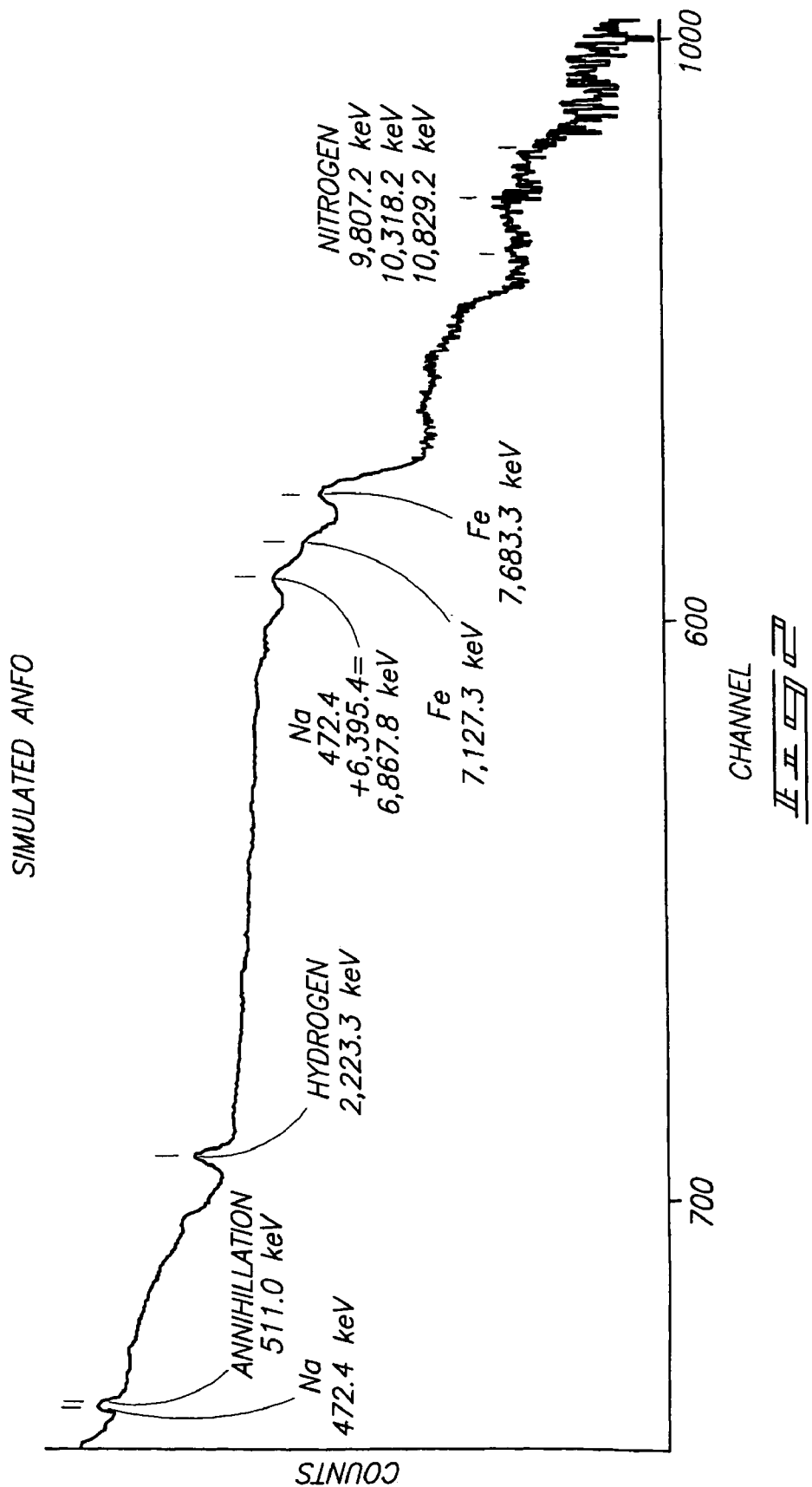
FIG. 2 is a graph showing an example of a typical sodium iodide spectrum on a simulated explosive.

Referring now to FIG. 2, a graphical depiction of a gamma-ray spectrum is provided with respect to a simulated explosive, ANFO. As seen therein, various peaks are identified with respect to this simulated ANFO explosive such as a sodium peak; a hydrogen peak; two iron peaks; and the several nitrogen peaks. In view of the amount of nitrogen which is present, the peak associated with the nitrogen is well defined. The associated KeV energy level for the nitrogen peaks are also shown. When presented with a typical gamma-ray spectrum as seen in FIG. 2, traditional and prior art detection methods which include Gaussian peak fitting, and other similar detection mechanisms are useful for identifying the nitrogen peaks as shown in this graphical depiction so as to provide a proper identification of the presence of an explosive.

Figure 3:
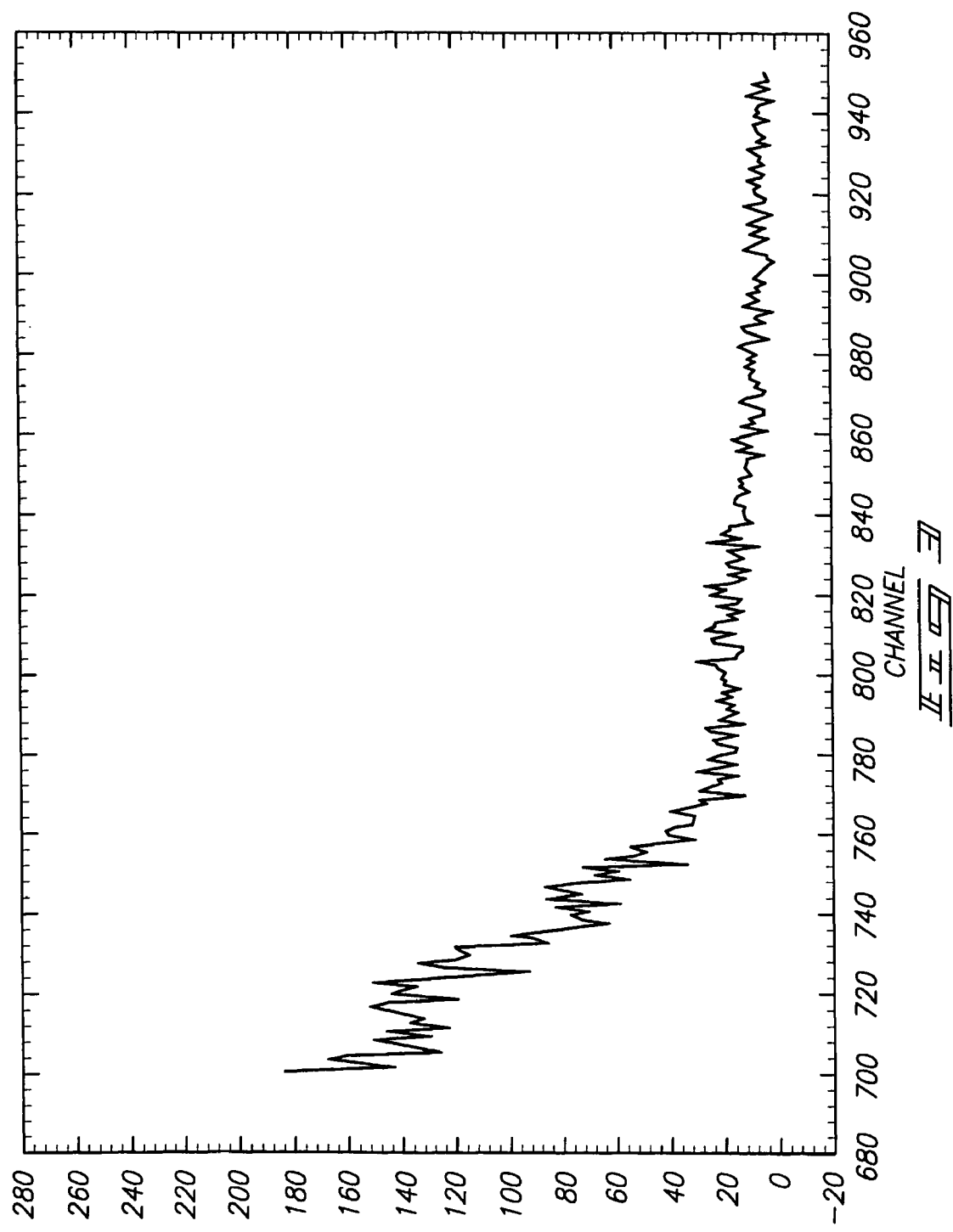
FIG. 3 is a graph illustrating a portion of a typical sodium iodide spectrum which shows the presence of a trace amount of a simulated explosive.

Referring now to FIG. 3, a partial gamma-ray spectrum is shown between channels 680 and 960 (280 channels in width) and which has multiple peaks. This figure shows a more typical gamma-ray spectrum as generated from a target 13 which has trace amounts of an element 14, nitrogen, incorporated in same, and which would potentially indicate the presence of an explosive. By studying and comparing FIG. 2 with FIG. 3, it will be recognized that the prior art techniques of Gaussian peak fitting, for example, which works well for specimens having a large amount of an element to be detected, such as nitrogen (FIG. 2), would not work adequately to identify the presence of trace amounts of nitrogen from this gamma-ray spectrum. The methodology of the present invention therefore provides a convenient means whereby a gamma-ray spectrum such as seen in FIG. 3, can be analyzed to determine the presence of trace amounts of elements of interest such as nitrogen in order to detect the presence of explosives, and the like.

Figure 4:
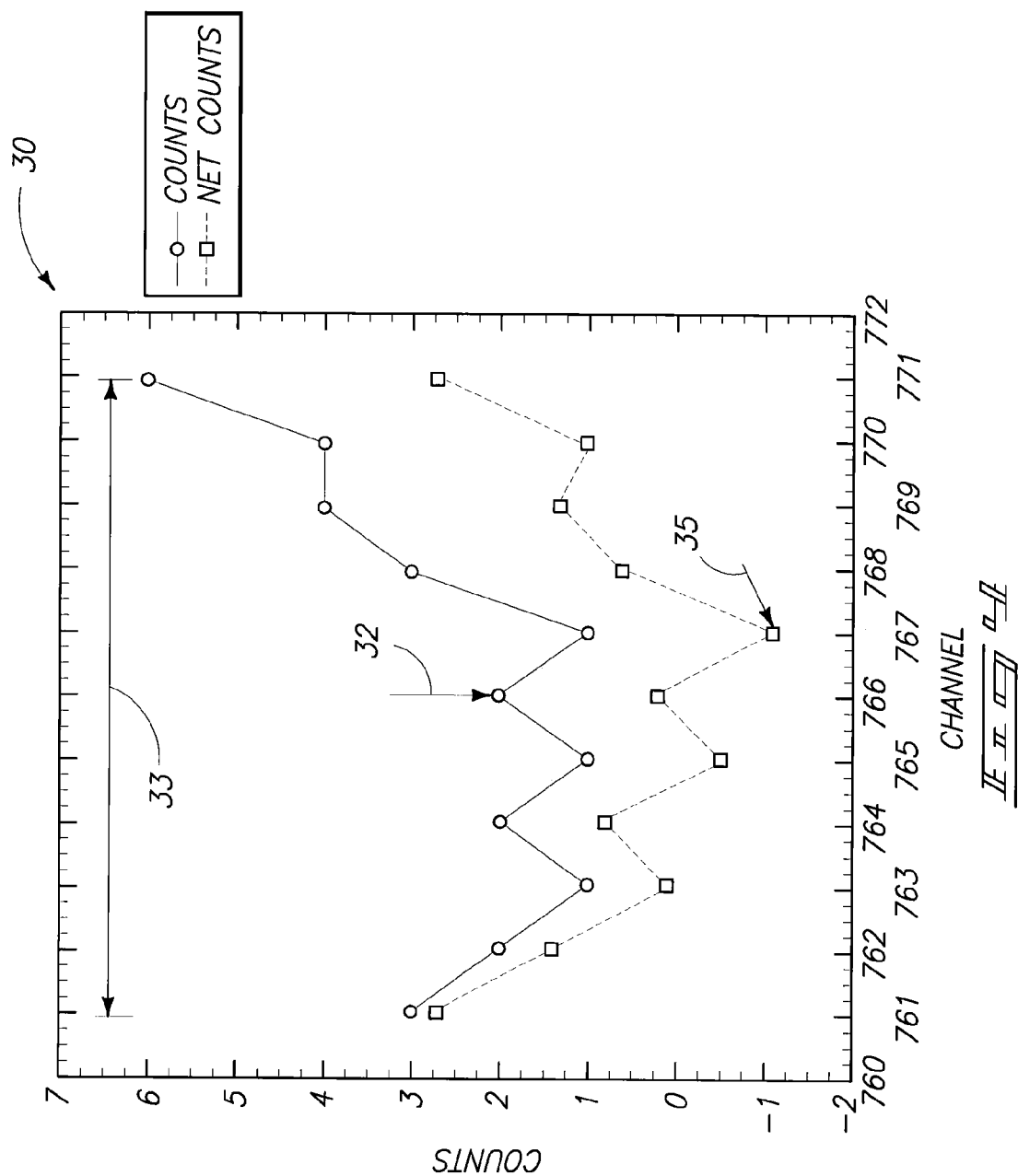
FIG. 4 is a graph illustrating a first aspect of the present invention.
Figure 5:
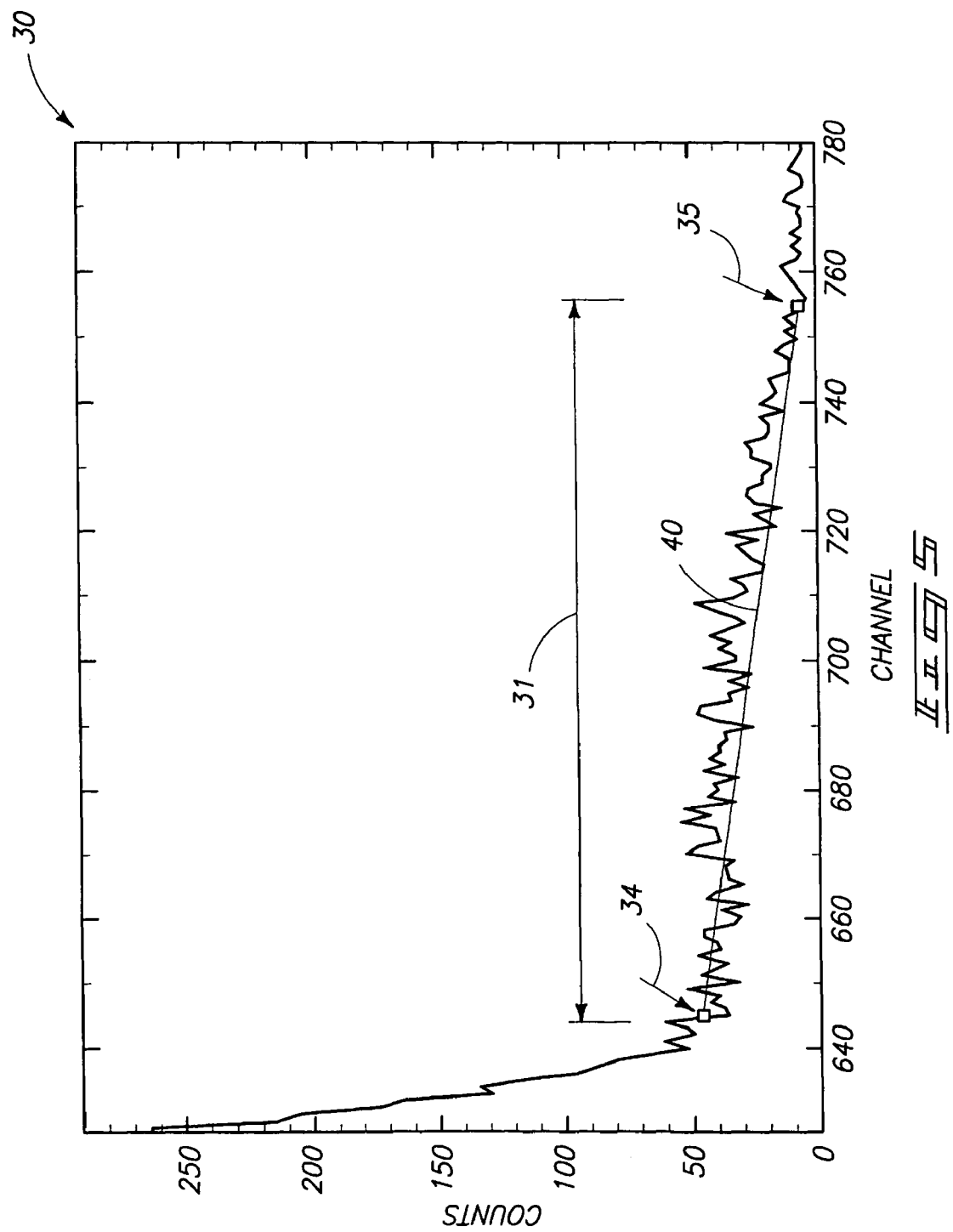
FIG. 5 is a graph illustrating a second aspect of the present invention.
Figure 6:
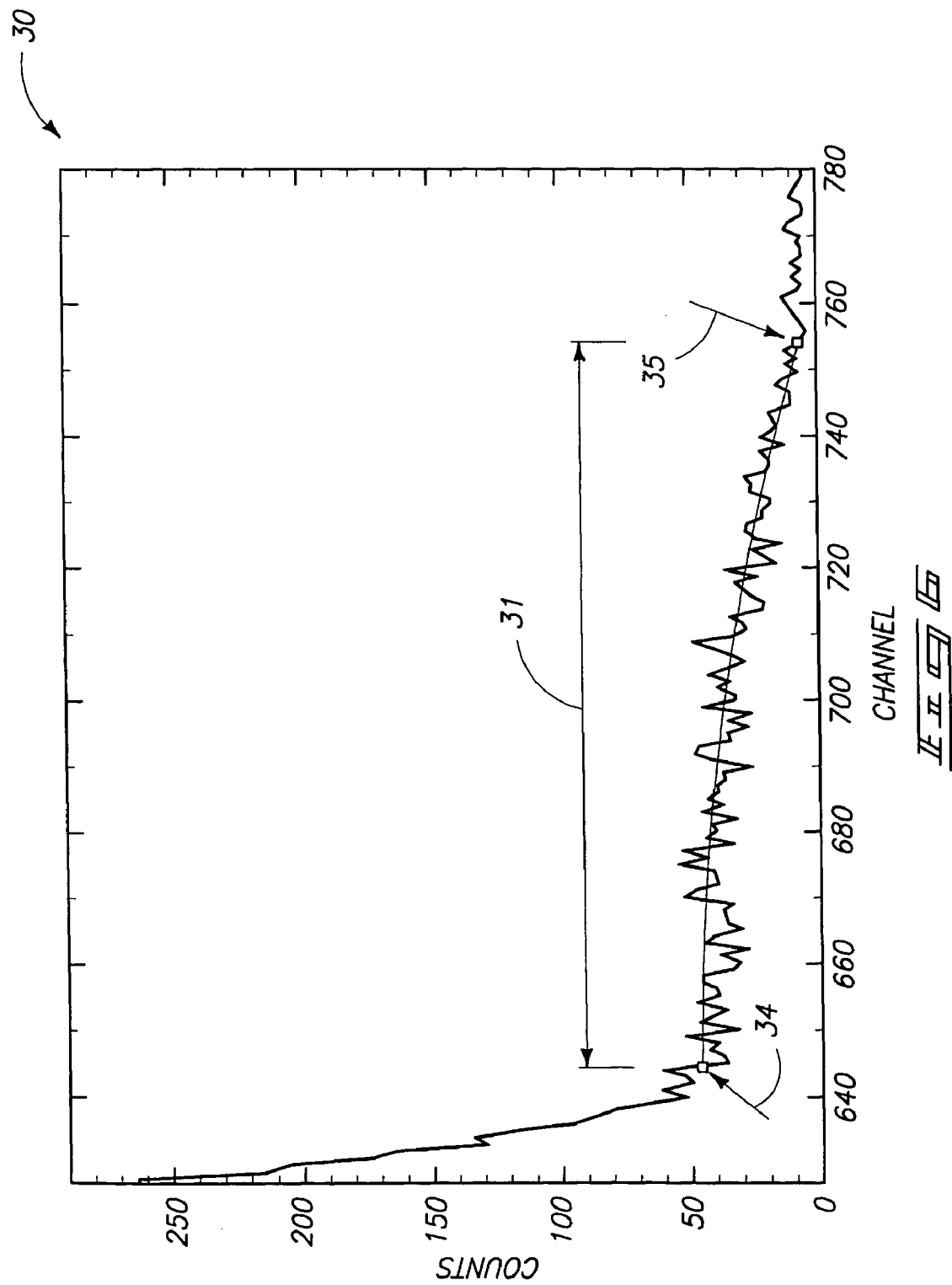
FIG. 6 is a graph illustrating a third aspect of the present invention.

Referring now to FIGS. 4, 5 and 6, the methodology as implemented by the present invention utilizes nonparametric assumptions about the shape of the gamma-ray spectrum 30 as provided by the digital electronics system 17. These nonparametric assumptions are selected from the group which include: (1) the shape of the gamma-ray spectrum has a non-Gaussian peak such as seen in FIG. 3; (2) the shape of the gamma-ray spectrum is defined by a number of counts above a linear background; this will be discussed in further detail with respect to FIG. 5; and (3) the shape of the gamma-ray spectrum is curved and is defined by a number of counts above a linear background such as seen by reference to FIG. 6. In the present methodology the method for detecting an element 14 includes a step of applying a statistical test to the shape of the gamma-ray spectrum 30 based upon the nonparametric assumptions to detect the small amount of the element to be detected. In this regard, the statistical test is selected from the group comprising a Z-test and a quadratic test, as will be discussed in greater detail hereinafter. As discussed, above, the two statistical tests are applied to the shape of the gamma-ray spectrum 30 as seen in FIGS. 4, 5 and 6 to determine the presence or absence of a small amount of the element to be detected, that being nitrogen, and which is typically incorporated in a number of different explosives.

As seen in FIGS. 4, 5 and 6, the methodology as employed on the gamma-ray spectrum 30 to detect the element of interest 14 includes as a first step of defining a region of interest 31 within the gamma-ray spectrum 30 and which corresponds with a small amount of the element to be detected. As seen in FIG. 5, for example, the region of interest 31 includes multiple ill defined peaks and has a channel width of more than 100 channels. The methodology includes another step of defining a search region 33 around an approximate last channel 32 (FIG. 4) of the region of interest 31, and which has a number of counts. As seen in that same view, the search region 33 covers a number of channels on either side of what will become the actual last channel of the region of interest 31 and which is indicated by the numeral 35 (FIG. 5). As illustrated in FIG. 4, there are two lines, one being the actual counts as provided for the various channels, and a second, dotted line which provides the adjusted counts for the same channels. In the present methodology, the minimum adjusted count on the second dotted line constitutes the actual last channel 35 of the region of interest 31. This methodology is similarly applied to locate the first channel of the region of interest, and which is generally indicated by the numeral 34. Alternatively, the last channel 35 (FIG. 5) is selected, at least in part, upon the location of the first channel 34. As seen by a study of FIGS. 4 and 5, the present methodology includes a step of selecting a plurality of channels having counts which are adjacent to the first channel 34 of the region of interest 31. For example, if the first channel 34 of the region of interest is channel 645, the methodology employs a step wherein the counts in channels 643 to 647 are then averaged to provide a low background channel count. Further, if the last channel 35 of the region of interest 31 constitutes channel 755, then a high background count is calculated by providing the average of the counts in channels 753 to 757, for example. Once these low and high background channel counts are calculated for each of the plurality of channels which are adjacent to each of the first and last channels, the methodology includes a step of selecting a height corresponding to the first 34 channel, and last channel 35 of the region of interest 31, and which are based, at least in part, upon the calculated averages; and further providing a line 40 (FIG. 5) which extends between the heights corresponding to the calculated averages of the first and last channels 34 and 35; and additionally calculating the slope of the line 40.

Referring now to FIG. 5, and wherein first channel 34 is 645, and the last channel 35 is 755, (110 channels in width) it will be appreciated that the background channel counts comprise that region underneath the line which is labeled 40. Still further, the total counts in the region of interest 31 is equal to the sum of the counts between the first channel 34 and the last channel 35. Further, the net channel counts equals the area above the line 40, and below the gamma-ray spectrum 30 as provided. Another way of defining net counts is that it equals the total counts, as defined above, minus the background counts. In the methodology as described above, the step of applying a statistical test to the shape of the gamma-ray spectrum 30 based upon the nonparametric assumptions further includes a step of calculating background counts in the region of interest 31 for the element to be detected based, at least in part, upon the number of counts in a plurality of channels which are located adjacent to the first channel 34 and the last channel 35 of the region of interest 31; and further calculating total counts in the region of interest 31. The methodology further includes a step of calculating net counts due to the element of interest by subtracting the background counts from the total counts in the region of interest; and further calculating a statistic from the net and background counts in the region of interest 31 for the element to be detected. The methodology further includes a step of calculating a probability value based upon the calculated statistic to derive a detection confidence factor which indicates the degree of assurance that the element is present. The methodology as described above comprises a Z-test which is one of the two statistical tests which is utilized to detect the element of interest 14.

As discussed earlier, one of the nonparametric assumptions about the shape of the gamma-ray spectrum is that the shape of the gamma-ray spectrum which has multiple ill defined peaks as seen clearly in FIGS. 5 and 6, and is defined by a number of counts above a linear background; and the shape of the gamma-ray spectrum is curved. This is best seen in FIG. 6. The methodology employs as one of its statistical tests, a quadratic test. In this regard, the methodology which applies this statistical test to the shape of the gamma-ray spectrum 30, as seen in FIG. 6, includes a step of fitting a quadratic equation, having a quadratic term, to the region of interest 31 which is defined between the first and last channels 34 and 35, respectively. The quadratic equation as seen in FIG. 6 is Y=−1591.9845+4.9535*X−0.038* $X^2$. The resulting statistical significance of the quadratic term of the quadratic equation, noted above (−0.038), determines the detection of the element of interest, that being nitrogen. In the methodology as described therefore, the method includes, following the step of fitting a quadratic equation having a quadratic term to the region of interest which is defined between the first and last channels, a further step of, calculating a statistical significance of the quadratic term which is derived from the quadratic equation, and further calculating a probability value for the statistical significance of the quadratic term to determine the presence of the element to be detected.

Referring still to FIG. 6, it will be understood, therefore, that a method for detecting an element of the present invention includes the steps of providing a gamma-ray spectrum 30; defining a region of interest 31, within the gamma-ray spectrum, and which corresponds with an element which is to be detected; defining a first channel 34 of the region of interest 31; defining a last channel 35 of the region of interest 31; fitting a quadratic equation having a quadratic term to the region of interest which is defined between the first and last channels; calculating a number of counts of a plurality of channels which are located adjacent to the first and last channels; calculating a statistical significance of the quadratic term which is derived from the quadratic equation; and calculating a probability value for the statistical significance of the quadratic term to determine a confidence value which relates to the presence of the element to be detected. In the present methodology the quadratic equation may include three quadratic terms. In the quadratic equation referenced above, the methodology further includes a step of utilizing a least squares regression method to fit the quadratic equation, having a quadratic term, to the region of interest 31. It should be understood that the least squares regression method may be weighted or unweighted. As noted earlier, the present methodology includes a step of using a statistical test which is selected from the group comprising a Z-test and a quadratic test. In this regard, the Z-test, as seen in FIGS. 4 through 6 includes a step of defining the first channel 34 of the region of interest 31, and further comprises the steps of determining an approximate first channel for the region of interest within the gamma-ray spectrum 30; and defining a search region in the vicinity of the approximate first channel, and which is defined by a number of channels on the opposite sides of the approximate first channel. This is seen by reference to FIG. 4. The methodology associated with the Z-test further includes the steps of calculating a slope of a line which extends along the search region; calculating an adjusted channel count value for each of the channels within the search region, and which is based, at least in part, upon the slope of the line; and selecting the first absolute minimum adjusted count value as the actual first channel 34 of the region of interest 31, as shown in FIGS. 5 and 6. The methodology further includes a step of selecting the last channel 35 based, at least in part, upon the selection of the first channel of the region of interest.

As understood by a study of FIG. 6, the method for detecting an element of the present invention includes the steps of providing a gamma-ray spectrum 30; defining a region of interest 31 within the gamma-ray spectrum which corresponds with an element 14 to be detected; defining a first channel 34 of the region of interest 31 which has a number of counts; defining a last channel 35 of the region of interest 31 which has a number of counts; fitting a quadratic equation, having a quadratic term, to the region of interest which is defined between the first and last channels 34 and 35; calculating a statistical significance of the quadratic term which is derived from the quadratic equation; calculating a probability value for the statistical significance of the quadratic term to determine the presence of the element to be detected; and comparing the probability value for the statistical significance of the quadratic term with the confidence factor to determine the presence of the element to be detected. In the methodology as described above, the step of calculating a probability distribution on the calculated statistic to derive the confidence factor is performed by the control system 22, and wherein the method further includes the steps of providing a standard Gaussian cumulative distribution function; and locating a point on the standard Gaussian cumulative distribution function which corresponds to the calculated statistic to derive the confidence factor. In the methodology as described above, the step of defining a region of interest 31 within the gamma-ray spectrum 30 is performed by the same control system 22, and wherein the method further includes the steps of defining an approximate last channel 32; defining a search region 33 which is positioned in the vicinity of the approximate last channel; calculating a slope of a line which extends through the search region 33 for the approximate last channel 32 of the region of interest 31; calculating an adjusted count value, for each of the channels in the search region, and which is based, at least in part, upon the calculated slope of the line; and selecting the first absolute minimum adjusted count value as the actual last channel 35 (FIGS. 5 and 6 of the region of interest. As earlier discussed, the first channel 34 (FIGS. 5 and 6) of the region of interest is based, at least in part, upon the selection of the last channel of the region of interest. As earlier discussed this same methodology could be reversed whereby the search region is located about the first channel 34.

OPERATION

The operation of the described embodiment of the present invention is believed to be readily apparent and is briefly summarized at this point.

The method for detecting an element of the present invention, and which is seen in FIGS. 1-6, respectively, includes as a first step, providing a gamma-ray spectrum 30; and defining a region of interest 31 within the gamma-ray spectrum 30 which corresponds with an element which is to be detected. The method further includes a step of defining an approximate first channel of the region of interest 31 and which has a number of counts; and defining a last channel 35 of the region of interest 31 which has a number of counts. The method further includes a step of calculating the number of counts of a plurality of channels which are located adjacent to the first and last channels 34 and 35 as seen in FIG. 5. The method further includes a step of calculating background counts in the region of interest 31 for the element to be detected based, at least in part, upon the number of counts in the plurality of channels which are located adjacent to the first and last channels. In the methodology as described, the method further includes the steps of calculating the total counts in the region of interest; and calculating net counts due to the element of interest by subtracting the background counts from the total counts in the region of interest. The method further includes the step of calculating a statistic from the net and background counts in the region of interest for the element to be detected; and calculating a probability value based upon the calculated statistic to derive a detection confidence factor indicating the degree of assurance that the element to be detected is present.

In the methodology as described above, the step of defining a search region for the approximate first channel of the region of interest 31 further includes the steps of calculating a slope of a line 40 which extends between the first and the last channels of the search region for the approximate first channel of the region of interest 31; calculating an adjusted count value, as seen in FIG. 4, for each of the channels within the search region, and which is based, at least in part, upon the slope of the line; and selecting the first channel within the search region which has an absolute minimum adjusted count value as the first channel 34 of the region of interest within the gamma-ray spectrum 30. With regards to the step for calculating a statistic from the net amount of the element to be detected, the methodology further includes the steps of providing a low background channel count for the region of interest, and wherein the low background channel count is the average of the number of counts in a plurality of channels which are adjacent to the first channel of the region of interest; and providing a high background count for the region of interest 31, and wherein the high background count is the average of the number of channel counts in a plurality of channels which are adjacent to the last channel 35 of the region of interest 31. Still further, the method includes a step of calculating a gross element amount based upon the sum of the number of channel counts in the respective channels between the low and high background channel counts; and further calculating an element background amount based upon the low and high background channel counts. With regards to the calculation of the net amount of the element to be detected, this methodology further includes utilizing the gross element amount of the element, and the element background amount, in the calculation of the net amount of the element detected. Still further, the step of calculating the statistic from the net amount of the element to be detected further comprises, at least in part, dividing the net amount of the element to be detected, by the averages of the low and high background channel counts, as earlier described. In the methodology as described above, the step of calculating the probability value is based, at least in part, upon the calculated statistic to derive a confidence factor, and wherein the method further includes the steps of providing a standard Gaussian cumulative distribution function; and identifying on the standard Gaussian cumulative distribution function a point which corresponds to the calculated statistic to derive the resulting confidence factor.

Therefore the present methodology as described above and which employs two tests which have been referred to herein as the Z-test and a quadratic test, and that are useful, when applied against a gamma-ray spectrum, as seen in the drawings, to detect small amounts of elements 14 which may indicate the presence of explosive substances in concealed locations within containers, vehicles and the like.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method for detecting an element, comprising:
providing a gamma-ray spectrum having multiple peaks of a target which may or may not have a small amount of a known element to be detected;
defining a region of interest within the gamma-ray spectrum which corresponds with the known element which is to be detected and which may or may not be present;
determining an approximate first channel for the region of interest within the gamma-ray spectrum;
defining a search region for the actual first channel of the region of interest, and which is defined by a number of channels on the opposite sides of the approximate first channel;
defining a first channel of the region of interest which has a number of counts;
defining a last channel of the region of interest which has a number of counts;
calculating the number of counts of a plurality of channels which are located adjacent to the first and last channels;
calculating background counts in the region of interest for the small amount of the element to be detected based, at least in part, upon the number of counts in the plurality of channels which are located adjacent to the first and last channels;
calculating the total counts in the region of interest;
calculating net counts due to the small amount of the element to be detected by subtracting the background counts from the total counts in the region of interest;
calculating a statistic from the net and background counts in the region of interest for the small amount of the element to be detected;
calculating a probability value based upon the calculated statistic to derive a detection confidence factor indicating the degree of assurance that the small amount of the element to be detected is present or absent;
providing a standard Gaussian cumulative distribution function;
identifying on the standard Gaussian cumulative distribution function a point which corresponds to the calculated statistic;
deriving the resulting confidence factor from the point which corresponds to the calculated statistic; and
displaying a message to an operator indicating the presence or absence of the element to be detected based, at least in part, upon the confidence factor.

2. A method as claimed in claim 1, and further comprising:
providing a neutron generator which generates a source of neutrons;
directing the source of neutrons at the target, and wherein the neutrons penetrate the target and interacts with the element to be detected to generate gamma-ray radiation; and
detecting the emission of the gamma-ray radiation to provide the gamma-ray spectrum.

3. A method as claimed in claim 1, and wherein after the step of defining the search region for the first channel of the region of interest, the method further comprises:
calculating a slope of a line which extends between the first and the last channels of the search region for the approximate first channel of the region of interest;
calculating an adjusted count value for each of the channels within the search region, and which is based, at least in part, upon the slope of the line; and selecting the first channel within the search region which has an absolute minimum adjusted count value as the first channel of the region of interest within the gamma-ray spectrum.

4. A method as claimed in claim 3, and wherein before the step of calculating a statistic from the net and background counts in the region of interest for the small amount of the element to be detected, the method further comprises:
providing a low background channel count for the region of interest, and wherein the low background channel count is the avenge of the number of counts in a plurality of channels which are adjacent to the first channel of the region of interest;
providing a high background count for the region of interest, and which is the average of the number of channel counts in a plurality of channels which are adjacent to the last channel of the region of interest;
calculating a gross element amount of the known element to be detected based upon the number of channel counts in the respective channels between the low and high background channel counts; and
calculating an element background amount based upon the low and high background channel counts.

5. A method as claimed in claim 4, and wherein the step of calculating the net counts due to the small amount of the element to be detected further comprises, utilizing the gross element amount of the element and the element background amount in the calculation.

6. A method as claimed in claim 5, and wherein the step of calculating the statistic from the net count in the region of interest for the small amount of the element to be detected further comprises, at least in part, dividing the net count in the region of interest for the small amount of the element to be detected, by the averages of the low and high background channel counts.

7. A method for detecting an element, comprising:
providing a gamma-ray spectrum derived from a target which encloses a small amount of an element to be detected and which may or may not be present;
defining a region of interest having multiple peaks within the gamma-ray spectrum which corresponds with the element to be detected;
defining a first channel of the region of interest by determining an approximate first channel for the region of interest within the gamma-ray spectrum;
defining a search region in the vicinity of the approximate first channel for the region of interest, and which is defined by a number of channels on the opposite sides of the approximate first channel;
defining a last channel of the region of interest;
fitting a quadratic equation, utilizing a least squares regression method which is weighted or unweighted and which has a quadratic term, to the region of interest which is defined between the first and last channels;
calculating a statistical significance of the quadratic term which is derived from the quadratic equation;
calculating a probability value for the statistical significance of the quadratic term to determine a confidence value which relates to the presence or absence of the small amount of the element to be detected; and
displaying a message to an operator indicating the presence or absence of the small amount of the element to be detected.

8. A method as claimed in claim 7, and further comprising:
providing a neutron generator which generates a source of neutron energy;
directing the source of neutron energy at the target, and wherein the neutron energy penetrates the target and interacts with the element to be detected to generate gamma-ray radiation; and
detecting the emission of the gamma-ray radiation to provide the gamma-ray spectrum.

9. A method as claimed in claim 7, and further comprising:
calculating a slope of a line which extends along the search region;
calculating an adjusted channel count value for each of the channels within the search region, and which is based, at least in part, upon the slope of the line;
selecting a first absolute minimum adjusted count value as the first channel of the region of interest; and
selecting the last channel of the region of interest based, at least in part, upon the selection of the first channel of the region of interest.

10. A method as claimed in claim 7, and wherein the element to be detected is nitrogen which may be incorporated into an explosive substance, and wherein the target comprises a container and/or a vehicle which conceals the explosive substance.

11. A method as claimed in claim 8, and further comprising:
positioning the neutron generator at a stand-off distance from the target;
providing a gamma-ray energy detector, and positioning the gamma-ray energy detector at a detection distance from the target, and wherein the gamma-ray energy detector generates an electrical output when exposed to gamma-ray radiation;
providing a digital electronics system which is electrically coupled with the each of the neutron generator and the gamma-ray energy detector, and which produces an electrical output; and
employing a control system to cause the neutron generator to generate neutrons, receive the electrical output of the digital electronics system, and display the message to the operator, and wherein digital electronics system provides the gamma-ray spectrum, at least in part, from the electrical output of the gamma-ray energy detector.

* * * * *